United States Patent [19]

Suzuki

[11] Patent Number: 4,655,941

[45] Date of Patent: Apr. 7, 1987

[54] METHOD OF PREPARING MIXED ELECTROLYTE POWDER FOR BICARBONATE DIALYSIS AND POWDER MIXTURE FORMED

[75] Inventor: Takeshi Suzuki, Tokushima, Japan

[73] Assignee: Tomita Pharmaceutical Corp., Ltd., Japan

[21] Appl. No.: 789,965

[22] PCT Filed: Jan. 13, 1984

[86] PCT No.: PCT/JP84/00042

§ 371 Date: Oct. 1, 1985

§ 102(e) Date: Oct. 1, 1985

[87] PCT Pub. No.: WO85/03435

PCT Pub. Date: Aug. 15, 1985

[51] Int. Cl.$^4$ ..................... C09K 3/00; B01D 13/00
[52] U.S. Cl. ......................... 252/1; 252/189; 252/190; 252/193; 23/303; 210/96.2; 210/321.3; 422/902; 159/48.1
[58] Field of Search ............. 252/193, 1, 182, 189, 252/190; 23/303; 210/96.2, 321.3, 645–647; 422/902; 159/48.1

[56] References Cited

U.S. PATENT DOCUMENTS

| | | | |
|---|---|---|---|
| 3,112,239 | 11/1963 | Andermatt | 159/48.1 X |
| 3,196,930 | 7/1965 | Ebert et al. | 159/48.1 |
| 3,560,380 | 2/1971 | Stade | 252/1 |
| 3,882,020 | 5/1975 | Cere | 210/96.2 X |
| 3,962,075 | 6/1976 | Fialkoff et al. | 210/647 X |
| 4,202,760 | 5/1980 | Storey et al. | 210/96.2 X |
| 4,292,227 | 9/1981 | Michaels et al. | 210/646 X |
| 4,336,881 | 6/1982 | Babb et al. | 252/1 X |
| 4,489,535 | 12/1984 | Veltman | 252/1 X |

FOREIGN PATENT DOCUMENTS 515  3/1981  World Int. Prop. O. .......... 210/645

Primary Examiner—John F. Terapane
Assistant Examiner—Matthew A. Thexton
Attorney, Agent, or Firm—Larson and Taylor

[57] ABSTRACT

A method of producing a mixed electrolyte powder having an electrolyte ion composition suited for use in preparing a dialyzing fluid for perfusing artificial kidney systems for bicarbonate dialysis, which method comprises a step of pulverizing the whole or part of sodium chloride, which is one of the components of the above powder, in a micronizer to a microfine powder having a particle size of about 20–30 μm and adding thereto 2–4 percent by weight of glacial acetic acid by spraying, whereby a microfine powder of sodium chloride acidified with acetic acid is obtained, a step of dissolving other components constituting the above mixed powder and, if any, the remaining portion of sodium chloride in warm water and spray-drying the solution using a spray nozzle or disk atomizer to a microfine powder having a particle size of about 20–100 μm, and a step of mixing both the microfine powders obtained in the above steps together.

8 Claims, No Drawings

METHOD OF PREPARING MIXED ELECTROLYTE POWDER FOR BICARBONATE DIALYSIS AND POWDER MIXTURE FORMED

TECHNICAL FIELD

This invention relates to a method of preparing a mixed electrolyte powder for bicarbonate dialysis (dialysis using a bicarbonate-containing dialyzing fluid) and, more particulary, to a method of preparing a novel mixed electrolyte powder with which a specific electrolyte ion composition and an appropriate pH can be secured always in a constant manner through mere dissolution thereof in water and thereby an electrolyte solution for perfusing artificial kidney systems for bicarbonate dialysis can be prepared.

BACKGROUND ART

The bicarbonate-containing artificial perfusing fluid is one of the dialyzing fluids for perfusing artificial kidney systems and generally comprises a concentrated aqueous solution of various electrolytes necessary for hemodialysis (composition A) and a concentrated aqueous solution of sodium bicarbonate powder alone or in combination of part of the above-mentioned electrolytes (e.g. NaCl, $CH_3COONa$) (composition B). These compositions are placed in the respective tanks of an artificial kidney system for bicarbonate dialysis and, at the time of use, they are diluted with water and mixed together to give a dialyzing fluid. Such dialyzing fluid, which contains sodium bicarbonate (as composition B) originally known to be a factor directly adjusting the body fluid pH and hence physiologically adequate, efficiently and rapidly improves the acid-base balance in metabolic acidosis, respiratory alkalosis and the like, does not provoke indefinite complaints, such as hypotension and nausea, during dialysis, and can accomplish rapid dehydration. Therefore, said fluid is much expected to be effective and safe in the treatment of hyperpotassemia, hypocalcemia, hyperphosphoremia and hyperaceta, for instance, and especially in large-area short-time dialysis.

However, the above-mentioned sodium bicarbonate is low in solubility and unstable against acid pH and heat. Accordingly, it has the fatal disadvantage that, in preparing dialyzing fluids by admixing it with composition A and during storage of said fluids, it generates carbon dioxide gas and thereby causes increase of pH and decrease of carbon dioxide gas pressure, whereby calcium and magnesium in composition A precipitate out in the form of carbonate. Therefore, in preparing the above-mentioned bicarbonate-containing dialyzing fluids, the prior art used the technique of introducing carbon dioxide gas into the mixing tank (reaction vessel) to thereby compensate the loss of carbon dioxide gas due to escape and thus maintain the pH of the dialyzing fluids at or around the neutral pH or the technique of adding an appropriate amount of a mineral acid or organic acid to the above reaction vessel or composition A to thereby adjust the pH. However, these procedures themselves are rather complicated or troublesome and, in addition, highly precise concentration and pH control is required. Moreover, the above composition A itself is a concentrated solution, so that its storage stability cannot be secured, namely pH changes with the lapse of time, for example during storage, are unavoidable. The large volume and weight of such solution are its further disadvantages in its handling, such as transportation.

It is an object of the present invention to provide a method of producing a uniform-quality powder-form composition A for preparing bicarbonate-containing dialyzing fluids, which can be produced in an easy manner and on a commercial scale and in which necessary electrolyte ions are in a very uniformly mixed state without substantial variation in composition, and thereby solve not only the problems hitherto encountered in preparing bicarbonate-containing dialyzing fluids but also the stability and handling problems.

DISCLOSURE OF THE INVENTION

The present invention provides a method of producing a mixed electrolyte powder having an electrolyte ion composition suited for use in preparing a dialyzing fluid for perfusing artificial kidney systems for bicarbonate dialysis, which method comprises a step of pulverizing the whole or part of sodium chloride, which is one of the components of the above powder, in a micronizer to a microfine powder having a particle size of about 20–30 $\mu$m and adding thereto 2–4 percent by weight of glacial acetic acid by spraying, whereby a microfine powder of sodium chloride acidified with acetic acid is obtained, a step of dissolving other components constituting the above mixed powder and, if any, the remaining portion of sodium chloride in warm water and spray-drying the solution using a spray nozzle or disk atomizer to a microfine powder having a particle size of about 20–100 $\mu$m, and a step of mixing both the microfine powders obtained in the above steps together.

In accordance with the invention, a mixed electrolyte powder very useful as composition A for bicarbonate dialysis can be produced. A desired pH value can be obtained by mere dissolution of said powder in water.

An advantageous feature of the invention consists in that the powder product obtained by using the above-mentioned microfine powder of sodium chloride acidified with acetic acid, when dissolved in water for use as composition A, gives an adequate pH and therefore will not cause any abnormal carbon dioxide gas generation, any decrease in carbon dioxide pressure, any local pH increase or the like or will not incur any substantial risk of causing precipitation of calcium or magnesium in the form of carbonate.

Another advantageous feature of the invention lies in that, irrespective of specific gravity differences, the necessary electrolyte components of the above-mentioned composition A, including in particular KCl which is a trace component, can be made up into a homogeneous microfine powder uniform in particle size by spray-drying an aqueous solution of said components. The microfine powder consists of minute spherical particles each having a constant specified composition, is nonhygroscopic and stable and, furthermore, is close in particle size to acetic acid-acidified sodium chloride to be mixed therewith, so that these can be mixed together very easily.

A third advantageous feature of the invention is that, owing to the above second advantage, such powder product which is composed of particles constant in electrolyte composition and uniform in size can be produced in a large quantity at a time by a simple and easy mixing procedure. Whereas it is in general difficult to mix two or more components differing in particle size to a homogeneous powder and such mixing becomes still more difficult especially when the components are to be mixed in widely different proportions and on a large scale, no such difficulties are encountered with the method of the present invention. The powder product obtained in accordance with the invention, when distributed in packagings, does not reveal any substantial variation in electrolyte composition among batches.

It is a further advantage of the method of the invention that, since it occurs as a powder, the product, when packed in a hermetically sealed condition, can be stored, transported and otherwise handled in a simple and easy manner and can stably retain its constant quality during a prolonged period of time, without substantial changes in quality, such as changes in pH.

When the mixed powder obtained by the method of the invention is used, it is possible to prepare, very easily, bicarbonate-containing dialyzing fluids always constant and adequate in pH, electrolyte composition, carbonate ion concentration, carbon dioxide gas pressure and other respects. The bicarbonate-containing dilyzing fluids thus prepared of course produce their particular, excellent effects in hemodialysis, such as improvement of metabolic acidosis or reduction in the frequency of indefinite complaints, and the above effects become more remarkable especially because the dialyzing fluid preparation is easy and there occurs no great variation in quality.

In the method of the present invention, it is essential to use an acetic acid-acidified sodium chloride powder treated in a special manner. As the sodium chloride material to be used in carrying out said method, there is used that sort of sodium chloride which is listed in the Japanese Pharmacopeia, occurs as crystals or a crystalline powder, contains not less than 99.5% of NaCl and generally has a particle size of about 500–600 $\mu$m. In accordance with the invention, such sodium chloride is pulverized to a particle size of about 20–30 $\mu$m using a micronizer. Although the kind of micronizer is not critical, that type with which pulverization and classification can be realized simultaneously and a fraction having the desired particle size can be separated out is preferred. The rotor speed can be suitably within the range of 7,000–8,000 rpm (revolutions per minute) and the separator speed within the range of 2,000–3,000 rpm. The particle size of the sodium chloride prepared in the above manner should be within the range of about 20–30 $\mu$m. Such sodium chloride powder can retain its favorable powder condition even after the subsequent addition of glacial acetic acid by spraying.

In accordance with the invention, glacial acetic acid is added to the above microfine sodium chloride powder by spraying. The spraying is performed in an appropriate vessel such as a rotary stirrer vessel. As the glacial acetic acid, there is used glacial acetic acid containing not less than 99.0% of $CH_3COOH$ (60.05) and meeting the requirements of Japanese Pharmacopeia or JIS (Japanese Industrial Standard) for special reagent grade glacial acetic acid. More detailedly, the spraying can be conducted using a pressure nozzle set in the central part of a rotary stirrer vessel, for instance. The amount of glacial acetic acid to be added by spraying is within the range of 2–4 percent by weight based on the sodium chloride weight. The acetic acid-acidified sodium chloride obtained by the addition of glacial acetic acid in said amount can hold its powder condition, and the mixed electrolyte powder of the invention obtained by using such sodium chloride, when dissolved in water in preparing composition A for the preparation of bicarbonate-containing dialyzing fluids, allows said composition A to have an ideal pH value, namely a pH of about 4.5. The good flowability of the acetic acid-acidified sodium chloride powder thus obtained is presumably due to the phenomenon that a huge number of very minute sodium chloride particles are adsorbed on each of glacial acetic acid droplets sprayed in the manner of mist, resulting in the above powder each particle of which is composed of such group of microfine sodium chloride particles and said acetic acid droplet surrounded by said particles. Anyhow, the powder obtained remains stable and retains its flowability for a long period of time and can be admixed with other powders without any drying in advance.

As the other electrolytes to be mixed in powder form with the acetic acid-acidified sodium chloride powder obtained in the above process, there may be used compounds conventionally used as the material for preparing dialyzing fluids, more specifically potassium chloride (KCl), calcium chloride ($CaCl_2.2H_2O$), magnesium chloride ($MgCl_2.6H_2O$) and sodium acetate ($CH_3COONa$ or $CH_3COONa.3H_2O$), each listed on the Japanese Pharmacopeia, Japanese Food Additives Standards, or JIS (for reagents). These electrolytes are dissolved in warm water and the solution is spray-dried to a microfine powder about 20–100 $\mu$m in particle size using a spray nozzle or disk atomizer. The above warm water preferably has a temperature of about 35°–40° C. The dissolution is generally carried out with stirring. The aqueous solution obtained is preferably an aqueous solution concentrated as much as possible. A concentration of about 35% is generally as appropriate one.

The spray drying of the above warm aqueous solution is performed using a spray nozzle or disk atomizer. The spray drying conditions are selected such that a microfine powder having a particle size of about 20–100 $\mu$m can be obtained. As the spray nozzle, there is preferably used a nozzle having an orifice diameter of about 1.0–2.0 mm. The disk atomizer is rotated preferably at a speed of about 10,000–30,000 rpm. The spray drying temperature conditions are such that the temperature at the inlet to the drying chamber is generally about 200°–400° C., preferably about 350°–400° C., and the outlet temperature is generally about 100°–200° C., preferably about 150°–200° C. The liquid-sending pump pressure in spray drying may be selected in an optional manner with 10 kg/cm² as the general standard. The drying time required is generally very short and the desired mixed powder can be obtained in several seconds to several tens of seconds.

The mixing ratio among the electrolytes to be spray-dried in the above process is selected such that bicarbonate-containing dialyzing fluids prepared by dissolving in water the spray-dried powder thus obtained and the previously mentioned, acetic acid-acidified sodium chloride powder, followed by mixing the solution with composition B ($NaHCO_3$ solution) have the following ion composition:

| | |
|---|---|
| $Na^+$ | 135–140 mEq/l |
| $K^+$ | 0–4.0 mEq/l |
| $Ca^{2+}$ | 2.5–3.5 mEq/l |
| $Mg^{2+}$ | 1.0–1.5 mEq/l |
| $Cl^-$ | 106–107.5 mEq/l |
| $CH_3COO^-$ | 7–9 mEq/l |
| $HCO_3^-$ | 27.5–35 mEq/l |

The above CH$_3$COO$^-$ concentration is the total of the concentration of CH$_3$COONa or CH$_3$COONa.3H$_2$O (4-6 mEq/l as CH$_3$COO$^-$) from the spray-dried powder and that of CH$_3$COOH constituting the acetic acid-acidified sodium chloride powder.

The dialyzing fluids having the above ion composition preferably contain the electrolytes and NaHCO$_3$ in the following weight proportions:

| | |
|---|---|
| NaCl | 59.474-62.644% by weight |
| KCl | 1.157-1.998% by weight |
| CaCl$_2$.2H$_2$O | 0.978-2.738% by weight |
| MgCl$_2$.6H$_2$O | 0.676-1.634% by weight |
| CH$_3$COONa | 1.455-6.595% by weight |
| NaHCO$_3$ | 24.763-30.562% by weight |

The NaCl as one component of the above composition may wholly be in the acetic acid-acidified powder form. In that case, the mixed powder according to the invention (exclusive of composition B) preferably has the following composition:

| | |
|---|---|
| CH$_3$COOH—acidified NaCl | 83.263-88.887% by weight |
| KCl | 0-4.415% by weight |
| CaCl$_2$.2H$_2$O | 2.720-3.875% by weight |
| MgCl$_2$.2H$_2$O | 1.505-2.296% by weight |
| CH$_3$COONa | 4.048-8.767% by weight |

Alternatively, the above NaCl to be used in preparing the above composition may partly be in the acetic acid-acidified powder form, with the remaining portion being in the spray dried powder form. In this case, it is recommendable that the portion of NaCl converted to the acetic acid-acidified powder form should amount to 40-60 percent by weight, preferably about 50 percent by weight, based on the whole amount of the mixed powder according to the invention (composition A). This possibly facilitates the homogeneous mixing of said powder with the spray-dried powder.

When packed in a hermetically sealed condition, the mixture obtained in accordance with the invention can become a very easy-to-handle product retaining good preservability for a long period of time. Said product can be used directly as composition A for preparing bicarbonate-containing dialyzing fluids, the only requirement being to dissolve the same in an appropriate amount of water. The thus-obtained composition A can be expected to produce satisfactory effects without adding an additional portion of acid at the time of mixing with composition B or blowing carbon dioxide gas into the mixing vessel. In other words, the powder obtained in accordance with the invention, when dissolve in water in preparing dialyzing fluids, gives a solution (composition A) having an ideal pH value of about 4.5 and, on the other hand, composition B (aqueous solution) has a pH of about 8. Therefore, the resultant dialyzing fluids can have a pH of about 7.3 which is adequate for hemodialysis. The HCO$_3^-$ concentration in said dialyzing fluids is such that the pCO$_2$ value is maintained at a constant level of about 60 mmHg, which is adquate for the dialyzing fluids, as a result of the reaction between CH$_3$COOH in composition A and NaHCO$_3$ in composition B as shown in the following:

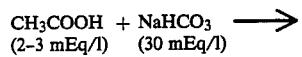
CH$_3$COOH + NaHCO$_3$
(2-3 mEq/l) (30 mEq/l)

-continued
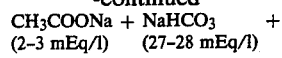
CH$_3$COONa + NaHCO$_3$ +
(2-3 mEq/l) (27-28 mEq/l)

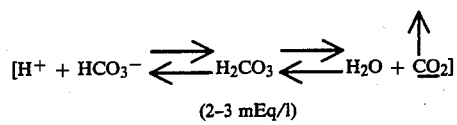
[H$^+$ + HCO$_3^-$ ⇌ H$_2$CO$_3$ ⇌ H$_2$O + CO$_2$]
(2-3 mEq/l)

The following examples illustrate the invention in further detail.

EXAMPLE 1

Potassium chloride (KCl) meeting the requirements of Japanese Pharmacopeia (26.24 kg), calcium chloride (CaCl$_2$.2H$_2$O) meeting the requirements of Japanese Pharmacopeia (36.22 kg), magnesium chloride (MgCl$_2$.6H$_2$O) of food additive grade (21.46 kg) and anhydrous sodium acetate (CH$_3$COONa) of food additive grade (40.48 kg) were dissolved in deionized water to make the whole volume 420 liters. With warming and stirring, the solution was led to a spray drier, where the solution was dried at an inlet temperature of 300° C.-350° C. while rotating a disk atomizer at a speed of 18,000 rpm. There was thus obtained a uniform, microfine powder (20-30 μm in particle size) containing the ions of the above-mentioned electrolytes.

Separately, Sodium chloride (NaCl) of Japanese Pharmacopeia grade (875.6 kg) was pulverized in a microanalyzer (8,000 rpm) until a microfine powder (about 20-30 μm in particle size) was obtained. This powder was stirred in a stirrer and thereto was added glacial acetic acid of Japanese Pharmacopeia grade (26.4 kg) by spraying. Thus was obtained a microfine sodium chloride powder acidified with acetic acid.

The previously mentioned microfine powder from the spray drier was introduced into the acetic acid-acidified, microfine sodium chloride powder, followed by stirring until homogeneity was attained. There was obtained a powder of the invention.

This powder product was used as composition A. Thus, it was hermetically packed in 2,486-g portions. Separately, sodium hydrogen carbonate (NaHCO$_3$) meeting the requirements of Japanese Pharmacopeia, as composition B, was hermetically packed in 882-g portions.

EXAMPLE 2

Sodium chloride (NaCl) of Japanese Pharmacopeia grade (375.6 kg), potassium chloride (KCl) of Japanese Pharmacopeia grade (26.24 kg), calcium chloride (CaCl$_2$.2H$_2$0) of Japanese Pharmacopeia grade (36.22 kg), magnesium chloride (MgCl$_2$.6H$_2$O) of food additive grade (21.46 kg) and anhydrous sodium acetate (CH$_3$COONa) of food additive grade (40.48 kg) were dissolved in deionized water to make the whole volume 1,500 liters. With warming and stirring, the solution was led to a spray drier, where it was dried by spraying under pressure form a spray nozzle having an orifice diameter of 1.2 mm at an inlet temperature of 300°-350° C. A homegeneous, microfine powder (50-100 μm in particle size) containing the ions of the above-mentioned electrolytes was obtained.

Separately, sodium chloride (NaCl) of Japanese Pharmacopeia grade (500 kg) was pulverized in a microanalyzer (8,000 rpm) to a microfine powder (about 20-30 μm). To this powder, there was added, with stirring in a stirrer, glacial acetic acid (CH₃COOH) of Japanese Pharmacopeia grade (26.4 kg) by spraying to give an acetic acid-acidified, microfine powder of sodium chloride.

Equal amounts of the above two microfine powders were mixed together until homogeneity was attained, to give a powder product according to the invention.

The powder product obtained, as composition A, was hermetically packed in 2,486-g portions. Separately, sodium hydrogen carbonate (NaHCO₃) of Japanese Pharmacopeia grade, as composition B, was hermetically packed in 882-g portions.

One pack of the composition A obtained either in Example 1 or in Example 2 was dissolved in water to make 10 liters to give solution A (pH about 4.5). One pack of the composition B (NaHCO₃ in each case) was dissolved in water to make 20 liters to give solution B (pH about 8.1). Both the solutions were charged into the main solution tank (for solution A) and aqueous bicarbonate tank (for solution B) of a bicarbonate-containing dialyzing fluid supplying apparatus (Nypro (Japan) model KH-20 AB). From the supplying tacks, they were fed to a mixing tank, where they were mixed and diluted with warm water (35°–40° C.) such that the total volume was made 350 liters. The mixed dilution was further sent to the terminal console, where the bicarbonate-containing dialyzing fluid was measured for respective electrolyte ion concentration, pH $PCO_2$ and $pO_2$. The results thus obtained are summarized below in Table 1 and Table 2. The Na⁺ and K⁺ ions were determined by using a flame photometer (Instrumentation Laboratories (USA) model 343), the HCO₃⁻ ion concentration, $pCO_2$ and $pO_2$ by using a gas analyzer (Instrumentation Laboratories model Micro 13 meter) and the Ca²⁺, Mg²⁺, CH₃COO⁻ and Cl⁻ ion concentrations by the methods respectively prescribed in the Japanese Pharmacopeia and Japanese Food Additives Standards.

TABLE 1

| Theoretical value | | Na⁺ | K⁺ | Ca²⁺ | Mg²⁺ | Cl⁻ | CH₃COO⁻ | HCO₃⁻ |
|---|---|---|---|---|---|---|---|---|
| Measured value | | 135 | 2.5 | 3.5 | 1.5 | 106.5 | 8–9 | 27–28 |
| Example 1 | No. 1 | 134.6 | 2.4 | 3.4 | 1.4 | 106.7 | 8.3 | 28.0 |
| | No. 2 | 135.2 | 2.5 | 3.5 | 1.5 | 107.4 | 8.4 | 27.2 |
| | No. 3 | 134.7 | 2.4 | 3.5 | 1.5 | 106.4 | 7.9 | 27.8 |
| | No. 4 | 135.3 | 2.5 | 3.4 | 1.4 | 107.3 | 8.3 | 27.3 |
| | No. 5 | 134.7 | 2.4 | 3.4 | 1.5 | 106.8 | 8.0 | 27.7 |
| Mean ($\bar{x}$) | | 134.90 | 2.44 | 3.44 | 1.46 | 106.92 | 8.18 | 27.60 |
| Example 2 | No. 1' | 135.2 | 2.5 | 3.5 | 1.5 | 106.8 | 8.4 | 27.5 |
| | No. 2' | 135.0 | 2.5 | 3.5 | 1.5 | 106.4 | 8.0 | 27.9 |
| | No. 3' | 135.1 | 2.5 | 3.4 | 1.5 | 106.7 | 8.3 | 27.3 |
| | No. 4' | 134.9 | 2.4 | 3.5 | 1.4 | 106.3 | 8.1 | 27.4 |
| | No. 5' | 134.9 | 2.5 | 3.4 | 1.5 | 106.4 | 8.3 | 27.8 |
| Mean ($\bar{x}$) | | 135.02 | 2.48 | 3.46 | 1.48 | 106.52 | 8.22 | 27.58 (mEq/l) |

TABLE 2

| Lot No. | | pH | $P_{CO_2}$(mmHg) | $P_{O_2}$(mmHg) | HCO₃⁻ (mEq/l) |
|---|---|---|---|---|---|
| Example 1 | No. 1 | 7.24 | 63.3 | 115.5 | 28.0 |
| | No. 2 | 7.30 | 60.7 | 116.0 | 27.2 |
| | No. 3 | 7.22 | 61.8 | 123.1 | 27.8 |
| | No. 4 | 7.26 | 59.4 | 119.4 | 27.3 |
| | No. 5 | 7.27 | 61.0 | 120.2 | 27.7 |
| Mean ($\bar{x}$) | | 7.26 | 61.24 | 118.84 | 27.60 |
| Example 2 | No. 1' | 7.25 | 62.7 | 122.7 | 27.5 |
| | No. 2' | 7.25 | 63.0 | 119.8 | 27.9 |
| | No. 3' | 7.23 | 61.8 | 118.2 | 27.3 |
| | No. 4' | 7.25 | 61.2 | 120.6 | 27.4 |
| | No. 5' | 7.26 | 62.2 | 121.2 | 27.8 |
| Mean ($\bar{x}$) | | 7.25 | 62.18 | 120.50 | 27.58 |

The above results indicate that, even in large-batch-size commercial production, the method of the invention can attain satisfactory mixture homogeneity with respect to the electrolyte ions and further that the solution prepared by mere dissolution in water holds a pH value suited for hemodialysis using a bicarbonate-containing dialyzing fluid, with good reproducibility, and holds a $pCO_2$ value of about 60 mmHg ($pCO_2$ being a factor for maintaining the HCO₃⁻ ion concentration at a level near the theoretical value).

The products of Example 1 and 2 were respectively packed in laminated aluminum foil bags (three-layered film; 12 μm polyethylene, 9 μm aluminum foil and 70 μm polyethylene), followed by sealing. Among the results of analysis performed immediately after production, 3 months later, 6 months later and 12 months later, there were noted no significant differences.

What is claimed is:

1. A method of producing a mixed electrolyte powder having an electrolyte ion composition suited for use in preparing a dialyzing fluid for perfusing artificial kidney systems for bicarbonate dialysis, which method comprises a step of pulverizing the whole or part of sodium chloride, which is one of the components of the above powder, in a micronizer to a microfine powder having a particle size of about 20–30 μm and adding thereto 2–4 percent by weight of glacial acetic acid by spraying, whereby a microfine powder of sodium chloride acidified with acetic acid is obtained, a step of dissolving other components constituting the above mixed powder and, if any, the remaining portion of sodium chloride in warm water and spray-drying the solution using a spray nozzle or disk atomizer to a microfine powder having a particle size of about 20–100 μm, and a step of mixing both the microfine powders obtained in the above steps together.

2. The method of claim 1, wherein the dialyzing fluid for perfusing artificial kidney systems for bicarbonate dialysis as prepared using said mixed powder contains 135–140 mEq/liter of Na⁺, 0–4.0 mEq/liter of K⁺, 2.5–3.5 mEq/liter of Ca²⁺, 1.0–1.5 mEq/liter of Mg²⁺, 106–107.5 mEq/liter of Cl⁻, 4–9 mEq/liter of CH₃COO⁻ and 27.5–35 mEq/liter of HCO₃⁻.

3. The method of claim 1, wherein said mixed electrolyte powder is composed of NaCl, KCl, $CaCl_2.2H_2O$, $MgCl_2.6H_2O$ and $CH_3COONa$ or $CH_3COONa.3H_2O$.

4. The method of claim 3, wherein the whole of the sodium chloride is converted to the form of a microfine powder acidified with acetic acid and said microfine powder is incorporated into said mixed electrolyte powder in an amount of 83.263–88.887 percent by weight.

5. The method of claim 3, wherein part of the sodium chloride is converted to the form of a microfine powder acidified with acetic acid and said microfine powder accounts for 40–60 percent by weight of said mixed electrolyte powder produced.

6. The method of claim 1, wherein the orifice diameter of the spray nozzle is 1.0–2.0 mm and the spray drying is performed at the inlet temperature of 200°–400° C.

7. The method of claim 1, wherein the spray drying is performed with a disk atomizer at a speed of rotation of 10,000–30,000 rpm.

8. A mixed electrolyte powder for bicarbonate dialysis as produced by the method of claim 1.

* * * * *